United States Patent [19]

Kelly

[11] Patent Number: 5,264,205
[45] Date of Patent: Nov. 23, 1993

[54] ORAL HYGIENE COMPOSITION

[75] Inventor: Mary H. Kelly, East Lyme, Conn.

[73] Assignee: Faria Ltd., New London, Conn.

[21] Appl. No.: 942,755

[22] Filed: Sep. 9, 1992

[51] Int. Cl.$^5$ .............................. A61K 7/16; A61K 7/20
[52] U.S. Cl. ........................................ 424/53; 424/49; 424/613; 424/616
[58] Field of Search ........................... 424/53, 613–616

[56] References Cited

U.S. PATENT DOCUMENTS

| | | | |
|---|---|---|---|
| 1,018,240 | 2/1912 | Foregger | 424/53 |
| 2,172,743 | 9/1939 | Taylor | 424/53 |
| 2,501,145 | 3/1968 | Smith | 424/53 |
| 3,574,824 | 4/1971 | Echeandia et al. | 424/50 |
| 3,988,433 | 10/1976 | Benedict | 424/53 |
| 4,582,701 | 4/1986 | Piechota | 424/52 |
| 4,837,008 | 6/1989 | Rudy et al. | 424/53 |
| 4,897,258 | 1/1990 | Rudy et al. | 424/53 |
| 4,971,782 | 11/1990 | Rudy et al. | 424/53 |
| 4,976,955 | 11/1990 | Libin | 424/53 |
| 4,980,154 | 12/1990 | Gordon | 424/53 |
| 4,988,560 | 1/1991 | Hunter et al. | 424/53 |
| 5,000,942 | 3/1991 | Libin | 424/53 |
| 5,084,268 | 1/1992 | Thaler | 424/53 |
| 5,122,365 | 6/1992 | Murayama | 424/49 |

Primary Examiner—Shep K. Rose
Attorney, Agent, or Firm—Hopgood, Calimafde, Kalil, Blaustein & Judlowe

[57] ABSTRACT

An oral hygiene composition in a suitably applicable form for whitening and cleaning teeth provides a non aqueous composition containing an oxygen releaser such as calcium peroxide, magnesium peroxide or potassium chlorate. The oxygen in these agents is stable in the composition until the composition meets water during actual brushing at which time the oxygen is released to effect a bleaching action removing stains from the surface of the teeth, thereby serving to whiten them. The composition may be formed with other known dental hygiene constituents providing for whitening and hygiene in one application.

11 Claims, No Drawings

ORAL HYGIENE COMPOSITION

FIELD OF THE INVENTION

The present invention relates to compositions for use in cleaning and brightening teeth, and more particularly, to low water compositions engineered for the controlled release of oxidizing reagents for cleaning stains off the dental surfaces in the oral cavity and combating dental plaque and bacteria.

1. Background of the Invention

The routine brushing of teeth after each meal is a customary practice by persons of almost all ages in our society. The purpose is twofold. First, brushing is considered an excellent form of preventive medicine. It is well established that continuous care by brushing will significantly extend the useful dental life for the practitioner, as both the incidence of cavity formation and gum disease are reduced. Second, and more often the primary driving force is the desire to obtain a bright smile, full of shining white teeth.

There has been tremendous research into compositions capable of preventing tooth decay, gum disease and other oral cavity ailments that have afflicted man through the ages. Concurrently, there has been a significant effort to develop techniques for brightening dental surfaces for basic cosmetic reasons. Although a variety of distinct approaches have been developed, none is considered ideal and the search continues. For example oxygen releasing agents such as peroxides have been used for dental whitening, but without an efficient delivery system for coordinated dental hygiene. Indeed, past efforts in using oxygen releasing agents routinely fail as the oxygen is often released prior to application on the teeth. The science of teeth bleaching is described in detail in a published reference entitled "Bleaching Teeth" by Feinman, Goldstein, and Garber published by Quintessence Publishing Co., Inc. This reference work provides a useful backdrop for the instant invention and its teachings are incorporated by reference as if set forth herein completely.

Outlined below are some of the salient prior art efforts in this technology.

2. Status of Prior Art

1. The dental use of oxygen to bleach teeth is detailed for dentists, in the book entitled "Bleaching Teeth", by doctors Feinman, Goldstein and Garber, published in 1987 (see above). There are a number of tooth whitening products on the market, the majority of them at this time consist of three components. The first is an acidic pre-rinse. The second is a gel containing usually hydrogen dioxide to be painted on the teeth. The third is a toothpaste.

2. It is believed that in the past several companies marketed an hydrogen peroxide gel composition for use separately from a conventional paste for regular tooth hygiene which of course requires a second somewhat duplicative treatment by the user with a true paste product.

3. Another treatment system type on the market has a container of toothpaste containing sodium bicarbonate alongside a container of gel containing hydrogen peroxide. These two are extruded simultaneously and then used directly to brush the teeth. The dual containers and dispensing system are much more costly than a toothpaste tube and more difficult to use in a routine fashion.

4. An attempt at providing a toothpaste which releases oxygen while brushing the teeth is shown in Smigel U.S. Pat. No. 4,405,559 (1982). Unfortunately the majority of the oxygen contained in this toothpaste is released during manufacture. Other patents are directed to similar goals:

5. Gordon U.S. Pat. No. 4,980,154 (1990): Encapsulates the calcium peroxide. The encapsulation of the calcium peroxide prevents the calcium peroxide from interacting with other ingredients and releasing its oxygen during manufacture or while residing in a packaging such as a tube ready for use. Unfortunately, while this method appears to be successful in preventing the breakdown of calcium peroxide before the product gets to the consumer, the encapsulation of the calcium peroxide is not broken down quickly enough during the normal brushing time of the average consumer, so that too little oxygen is released.

6. Fraser U.S. Pat. No. 4,980,152 (1990): Discloses a gel intended to be used as an oxygen releasing mouthwash. It is not however, a toothpaste that can be used in the normal manner.

7. Winston et al Patent No. 4,812,308: Discloses a tooth powder containing sodium bicarbonate and sodium percarbonate. This is an attempt to avoid the stability problems of producing an oxygen releasing toothpaste by using the more stable environment of a tooth powder.

The foregoing review of the prior art evidences a significant expenditure of resources in the search for a potent bleaching composition for use in dental care. The systems developed fail to address several key attributes required for broad appeal. Use of oxygen releasing agents often result in short shelf life as the tubes tend to burst from oxygen release pressure. Systems that are effective at releasing oxygen in the mouth cavity are inadequate for general purpose tooth care and dental hygiene. Heretofore, all efforts to efficiently combine these capabilities have resulted in overly expensive and complex systems or systems with significant drawbacks in practice. It was with this understanding of the problems of the prior art that formed the impetus for the present invention.

OBJECTS AND SUMMARY OF THE PRESENT INVENTION

It is an object of the present invention to provide a dental care product for whitening of teeth with the controlled release of an oxygen based bleaching agent.

It is also an object of the present invention to provide a composition for use as an everyday brushing agent in dental care that concurrently includes an oxygen releasing agent.

It is a further object of the present invention to provide a method of dental care that is routine and unburdensome while providing a powerful tooth whitening agent.

It is a further object of the present invention to provide a composition for the routine care of teeth through daily brushing that retains a bleaching agent through extended storage periods and releases this bleaching agent during brushing.

The above and other objects of the present invention are realized in specifically delineated composition formed as a paste and capable of use for daily dental brushing in accordance with traditional and customary practices. The composition comprises a low water admixture of a humectant, an abrasive, a surfactant, a binding agent and an active oxygen releasing agent such as calcium peroxide. The composition retains the active oxygen releasing components in a low water environment. During brushing, the addition of saliva with brushing turbulence triggers the release of oxygen and provides a vigorous scouring of residue and debris associated with dull and stained teeth, thereby revitalizing the appearance of the user's teeth.

In accordance with the varying aspects of the present invention, the compositions thereof are easily combined with the traditional components of tooth pastes such as one or more fluoride derivatives, including monofluorophosphate, as is per se well known in this art. The foregoing features of the present invention will be better understood via the description of illustrative examples thereof.

DESCRIPTION OF THE PRESENT INVENTION

The present INVENTION may be appreciated through the following discussion of the manufacture of the inventive compositions and specific examples of suitable compositions for use.

Method of Manufacture

The compositions herein are made using conventional mixing techniques. Care is taken, however, to control the temperature of the batch and to exclude water from the system. The exclusion of both water and a conventional gum changes the typical method of manufacture.

Applicability

The compositions of the present invention are used in a conventional manner.

The following examples further describe and demonstrate preferred embodiments within the scope of the present invention. The examples are given solely for the purpose of illustration and are not to be construed as limitations of this invention. Many variations thereof are possible without departing from the inventions spirit and scope.

EXAMPLE I

The following is a toothpaste representative of the present invention.

| Component | % |
|---|---|
| Glycerin 99% | 61.1 |
| Calcium Carbonate | 17.0 |
| Hydrated Silica | 16.0 |
| Titanium Dioxide | 1.0 |
| Calcium Peroxide (75% active) | 2.5 |
| Sodium Lauryl Sulfate | 1.4 |
| Flavor | 1.0 |
| | 100.0 |

The above composition was made in an Abbe mixer by adding 99% glycerin into a dry mixing vessel followed by the addition of titanium dioxide and flavor with moderate agitation. The calcium carbonate was then added while milling. The hydrated silica was then added while milling. The sodium lauryl sulfate was then mixed with vacuum. Calcium peroxide was added and the batch was mixed and milled under vacuum for about twenty minutes. The temperature of the batch was kept below 50 degrees Celsius.

EXAMPLE II

The following is a toothpaste representative of the present invention.

| Component | % |
|---|---|
| Glycerin 99% | 56.1 |
| Calcium Carbonate | 17.0 |
| Hydrated Silica | 16.0 |
| Titanium Dioxide | 1.0 |
| Magnesium Peroxide (25% active) | 7.5 |
| Sodium Lauryl Sulfate | 1.4 |
| Flavor | 1.0 |
| | 100.0 |

In the above examples, the carrier or humectant (e.g., glycerin) may be varied between 35 to 90 percent of the total composition without significant loss of its intended functionality. Also, other surfactants may be substituted, including sodium methyl cocoyl taurate, sodium lauryl sarcosinate and sodium lauryl sulfoacetate. Other suitable oxygen releasing agents include potassium chlorate, magnesium peroxide and calcium peroxide. The range of percent for the oxygen releasing agent is impacted by the activity of the agent. Other suitable abrasives include hydrated silica, calcium carbonate, dicalcium phosphate and alumina. Other whiteners include zinc oxide.

The above list is merely for illustration purposes and not meant to be exhaustive. A significant attribute discovered with the foregoing compositions is the oxygen stability in storage (tube) prior to use with a corresponding high oxygen activity in use during conventional brushing. These compositions may be combined with conventional dental paste ingredients such as fluoride (sodium fluoride and monofluorophosphate) without diminishing their effectiveness as a whitening agent. Although best results are obtained with minimum water, the water content may range up to 20 percent without significant loss in performance.

The above-described arrangement is merely illustrative of the principles of the present invention. Numerous modifications and adaptations thereof will be readily apparent to those skilled in the art without departing from the spirit and scope of the present invention.

I claim:

1. A water-free toothpaste dentrifice composition which is stable in storage and which releases oxygen while brushing consisting essentially of an admixture of:
   a. an oxygen releasing compound selected from the group consisting of inorganic peroxides and chlorate salts, ranging from 0.25 to 20 percent of the total weight of the composition;
   b. a humectant that is about 99 percent glycerin and essentially water free, ranging in percent between 35 to 90 percent of the total composition;
   c. an abrasive;
   d. a thickening or binding agent; and
   e. a detergent, wherein said composition has little or no added water.

2. The dentrifice of claim 1 where the humectant is glycerin.

3. The dentrifice of claim 1 where the thickening agent is hydrated silica or a hydrated silica abrasive having thickening properties.

4. The dentrifice of claim 1 where the oxygen releasing compound is calcium peroxide.

5. The dentrifice of claim 1 where the oxygen releasing compound is magnesium peroxide.

6. The dentrifice of claim 1 where the oxygen releasing compound is potassium chlorate.

7. The dentrifice of claim 1 where the thickening agent is a gum.

8. The dentrifice of claim 1 where the humectant is a glycol, such as polyethylene glycol.

9. The dentrifice of claim 1 where the abrasive is calcium carbonate.

10. The dentrifice of claim 1 where the abrasive is hydrated silica.

11. The dentrifice of claim 1 further containing a fluorine or fluoride releasing compound.

* * * * *